United States Patent
Whisler et al.

(10) Patent No.: US 11,389,198 B2
(45) Date of Patent: Jul. 19, 2022

(54) SYSTEM AND METHOD FOR MONITORING AND CONTROLLING INTRAUTERINE PRESSURE USING A PRESSURE CUFF

(71) Applicant: COVIDIEN LP, Mansfield, MA (US)

(72) Inventors: Jordan A. Whisler, Brookline, MA (US); Nikolai D. Begg, Wayland, MA (US)

(73) Assignee: Covidien LP, Mansfield, MA (US)

( * ) Notice: Subject to any disclaimer, the term of this patent is extended or adjusted under 35 U.S.C. 154(b) by 4 days.

(21) Appl. No.: 16/241,075

(22) Filed: Jan. 7, 2019

(65) Prior Publication Data
US 2020/0214742 A1    Jul. 9, 2020

(51) Int. Cl.
*A61B 17/42* (2006.01)
*A61B 17/135* (2006.01)
*A61B 5/022* (2006.01)

(52) U.S. Cl.
CPC ............ *A61B 17/42* (2013.01); *A61B 17/135* (2013.01); *A61B 5/022* (2013.01); *A61B 2017/4216* (2013.01)

(58) Field of Classification Search
CPC ....... A61B 17/42; A61B 17/135; A61B 5/022; A61B 2017/4216; A61B 1/303; A61B 5/033; A61B 5/03; A61M 2210/1433; A61M 2205/075; A61M 2205/3334; A61M 2205/3344; A61M 3/0233; A61M 3/0262; A61M 3/0216; A61M 3/022; A61M 3/0208; A61M 5/1483; A61M 1/0058
See application file for complete search history.

(56) References Cited

U.S. PATENT DOCUMENTS

| | | |
|---|---|---|
| 3,996,921 A | 12/1976 | Neuwirth |
| 4,295,631 A | 10/1981 | Allen |
| 4,759,349 A | 7/1988 | Betz et al. |
| 5,207,645 A | 5/1993 | Ross et al. |
| 5,308,335 A | 5/1994 | Ross et al. |
| 5,709,670 A | 1/1998 | Vancaillie et al. |
| 5,733,263 A | 3/1998 | Wheatman |
| 5,772,634 A | 6/1998 | Atkinson |
| 5,814,009 A | 9/1998 | Wheatman |
| 6,024,142 A | 2/2000 | Bates |
| 6,135,989 A | 10/2000 | Atad et al. |

(Continued)

OTHER PUBLICATIONS

Fournier, Basic Transport Phenomena in Biomedical Engineering, 2007, Taylor & Francis Group, Edition 2, 146-149 (Year: 2007).*

(Continued)

*Primary Examiner* — Brandy S Lee
*Assistant Examiner* — Hong-Van N Trinh
(74) *Attorney, Agent, or Firm* — Carter, DeLuca & Farrel LLP

(57) ABSTRACT

A method of determining a pressure of a body cavity with a controller of a fluid management system includes determining a pressure and a volume of a cuff disposed about a collapsible bag, determining a volume of the collapsible bag based on the pressure and the volume of the cuff, and determining a pressure of the collapsible bag based on the volume of the collapsible bag. The method also includes calculating a fluid flow from the collapsible bag into a body cavity from the collapsible bag and determining a pressure of the body cavity based on the fluid flow.

20 Claims, 7 Drawing Sheets

(56) References Cited

U.S. PATENT DOCUMENTS

| | | | |
|---|---|---|---|
| 6,641,556 B1 | 11/2003 | Shigezawa | |
| 7,031,602 B2 | 4/2006 | Faries, Jr. et al. | |
| 7,351,226 B1 | 4/2008 | Herskowitz | |
| 7,604,610 B2* | 10/2009 | Shener | A61M 3/0258 604/67 |
| 7,825,812 B2 | 11/2010 | Ogrin et al. | |
| 8,062,214 B2 | 11/2011 | Shener et al. | |
| 8,764,655 B2 | 7/2014 | Yoo | |
| 9,642,737 B2 | 5/2017 | Seres et al. | |
| 10,159,790 B2* | 12/2018 | Boyle | A61M 3/0216 |
| 2006/0047185 A1* | 3/2006 | Shener | A61B 17/3421 600/156 |
| 2007/0056983 A1 | 3/2007 | Wells | |
| 2010/0042074 A1* | 2/2010 | Weston | A61M 1/81 604/543 |
| 2010/0312039 A1* | 12/2010 | Quirico | G21F 3/00 600/4 |
| 2014/0194778 A1* | 7/2014 | Uziel | A61B 5/150221 600/578 |
| 2016/0220102 A1 | 8/2016 | Shener-Irmakoglu et al. | |
| 2017/0000946 A1 | 1/2017 | Boyle et al. | |
| 2017/0151403 A1* | 6/2017 | Higashiyama | A61M 16/202 |
| 2017/0205834 A1* | 7/2017 | Ambrosina | A61M 5/14224 |
| 2018/0207332 A1* | 7/2018 | Reever | A61M 1/0058 |

OTHER PUBLICATIONS

Extended European Search Report for Application 20150364.6 dated Jul. 6, 2020.

* cited by examiner

SYSTEM AND METHOD FOR MONITORING AND CONTROLLING INTRAUTERINE PRESSURE USING A PRESSURE CUFF

BACKGROUND

1. Technical Field

The present disclosure relates to systems and methods for performing medical procedures and, more specifically, to fluid management systems and methods for monitoring and controlling intrauterine pressure during medical procedures such as hysteroscopy.

2. Discussion of Related Art

Hysteroscopy is a medical procedure to examine the interior of the uterus. Hysteroscopy can be used to evaluate or treat conditions including, but not limited to, abnormal vaginal bleeding, polyps, tumors, anatomic abnormalities, scarring from previous surgical procedures, or retained placenta. In addition, hysteroscopy can be used to localize areas within the uterus for biopsy or treatment.

During hysteroscopy, an endoscope or a hysteroscope is inserted into the uterus through the vagina and the cervical opening. When the hysteroscope is disposed within the uterus, a fluid or gas is injected into the uterine cavity to distend the uterus and improve visualization. Throughout a hysteroscopy an intrauterine pressure is monitored to avoid over distending the uterus.

There is a continuing need for improved methods and systems for distending the uterus and monitoring the amount of fluid and pressure of the uterus during a medical procedure.

SUMMARY

This disclosure relates generally to systems for distending a body cavity and methods for determining a pressure within a distended organ.

In an aspect of the present disclosure, a method of determining a pressure of a body cavity with a controller of a fluid management system includes determining a pressure and a volume of a cuff disposed about a collapsible bag, determining a volume of the collapsible bag based on the pressure and the volume of the cuff, and determining a pressure of the collapsible bag based on the volume of the collapsible bag. The method also includes calculating a fluid flow from the collapsible bag into a body cavity from the collapsible bag and determining a pressure of the body cavity based on the fluid flow.

In aspects, determining a pressure of the cuff includes measuring a pressure of the cuff with a pressure sensor disposed between an air pump and the cuff. Determining a volume of the cuff may include monitoring an air flow into the cuff over time.

In some aspects, calculating the fluid flow from the bag includes subtracting the volume of the collapsible bag at a first time from a volume of the collapsible bag at a second time and dividing the result by the amount of time between the first and second time.

In particular aspects, wherein the method includes providing the pressure of the body cavity on a display of the controller. The method may include transmitting a control signal to the air pump to pump air into the cuff in response to determining a pressure of the body cavity.

In another aspect of the present disclosure, a method of determining a pressure of a body cavity with a fluid management system includes inflating a cuff to a predetermined pressure to apply pressure to a collapsible bag, monitoring a change in pressure of the cuff as fluid flows from the collapsible bag, and determining a bag volume change of the collapsible bag using the change in pressure of the cuff. The method also includes calculating a fluid flow from the collapsible bag into a body cavity from the collapsible bag and determining a pressure of the body cavity based on the fluid flow.

In aspects, inflating the cuff includes a controller activating an air pump to inflate the cuff to the predetermined pressure. Inflating the cuff may include manually pumping an air pump to inflate the cuff to the predetermined pressure.

In some aspects, the method includes releasing fluid from the collapsible bag after inflating the cuff to the predetermined pressure and monitoring the change in pressure of the cuff is done in response to releasing the fluid from the collapsible bag.

In particular aspects, a controller of the fluid management system determines the bag volume change from a memory of the controller. Inflating the cuff to a predetermined pressure may include measuring a pressure of the cuff with a pressure sensor disposed between an air pump and the cuff.

In certain aspects, calculating the fluid flow from the collapsible bag includes subtracting the volume of the collapsible bag at a first time from a volume of the collapsible bag at a second time and dividing the result by the amount of time between the first and second time. The method may include providing the pressure of the body cavity on a display of a controller. The method may include transmitting a control signal to an air pump to pump air into the cuff in response to determining a pressure of the body cavity.

In another aspect of the present disclosure, a fluid management system includes an air pump, a cuff, an air hose, a pressure sensor, and a controller. The cuff is configured to apply pressure to a collapsible bag. The air hose interconnects the air pump with the cuff. The pressure sensor is in communication with the air hose and is configured to generate a signal indicative of a pressure of the cuff. The controller is configured to receive the signal and to determine a pressure of a body cavity in response to the signal.

In aspects, the fluid management system includes a collapsible bag. The cuff may be configured to apply pressure to the collapsible bag as the cuff is inflated. The cuff may include a passage defined therethrough. The collapsible bag may be positioned within the passage of the cuff.

In some aspects, the air pump may be a manual air pump.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
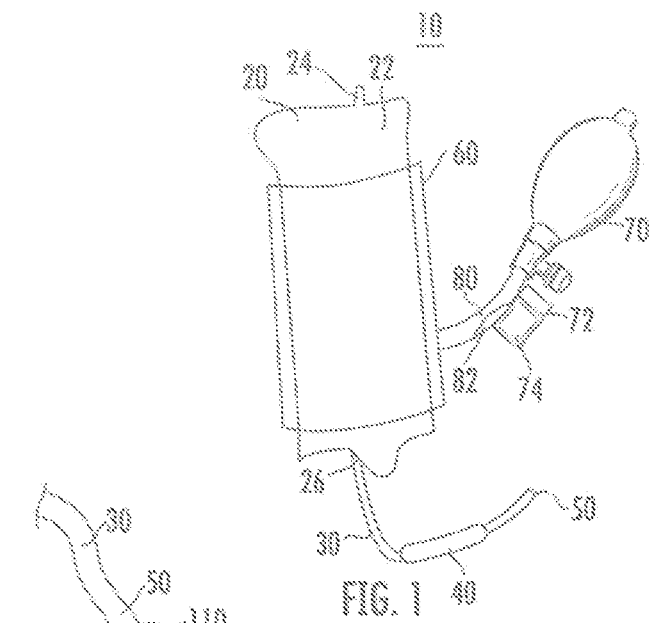
FIG. 1 is a perspective view of an exemplary fluid management system provided in accordance with the present disclosure.

Embodiments of the present disclosure are described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician.

Referring to FIG. 1, a fluid management system 10 includes a compressible bag 20, an output tube 30, a cuff 60, a pump 70, and an air hose 80. The fluid management system 10 is configured to provide fluid and maintain pressure to distend an organ during a medical procedure. As detailed below, the fluid management system 10 is described for use during a hysteroscopy procedure to distend a uterus. This description should not be seen as limiting as the fluid management system 10 may be used to provide fluid and maintain pressure to distend a plurality of distendable organs during a variety of medical procedures.

The compressible bag 20 includes a fluid reservoir 22 defined therein that is configured to hold a volume of fluid. The compressible bag 20 includes an output port 26 that is coupled to the output tube 30 such that a channel (not shown) of the output tube 30 is in fluid communication with the fluid reservoir 22 of the compressible bag 20. The compressible bag 20 may include a hanger 24 on an opposite side from the output port 26 that is configured to support the compressible bag 20, e.g., on a hook. The hanger 24 may include a scale integrated into the compressible bag 20.

The output tube 30 extends to an outlet 50 and may include a safety valve 40. The safety valve 40 may be an inline valve that prevents overpressurizing the output tube 30. For example, the safety valve 40 may be a relief valve that vents fluid to prevent overpressurizing the output tube 30.

The cuff 60 is disposed about the compressible bag 20 and is configured to compress the compressible bag 20 to reduce a volume of the fluid reservoir 22 and/or increase a pressure of the fluid reservoir 22. The cuff 60 is in fluid communication with the air pump 70 via the air hose 80. The air pump 70 is configured to inflate the cuff 60 to compress the compressible bag 20. The air pump 70 may be a compressible bulb that is squeezable by a clinician such that each squeeze pumps an amount of air from the environment into the air hose 80. In some embodiments, the air pump 70 is an electric air pump which pumps air from the environment through the air hose 80. The cuff 60 may form a ring about the compressible bag 20, similar to a blood pressure cuff on an arm, or the cuff 60 may completely surround the compressible bag 20. In embodiments, the cuff 60 is a bladder that is disposed on one side of the compressible bag 20 and is configured to press the compressible bag 20 against a fixed surface such that a volume of the fluid reservoir 22 is reduced and/or pressure within the fluid reservoir 22 is increased.

For a detailed description of a suitable compressible bag and cuff reference may be made to U.S. Patent Publication No. 2017/0000946 and U.S. Pat. No. 8,062,214, the entire contents of each of these publications are hereby incorporated by reference.

Figure 2:
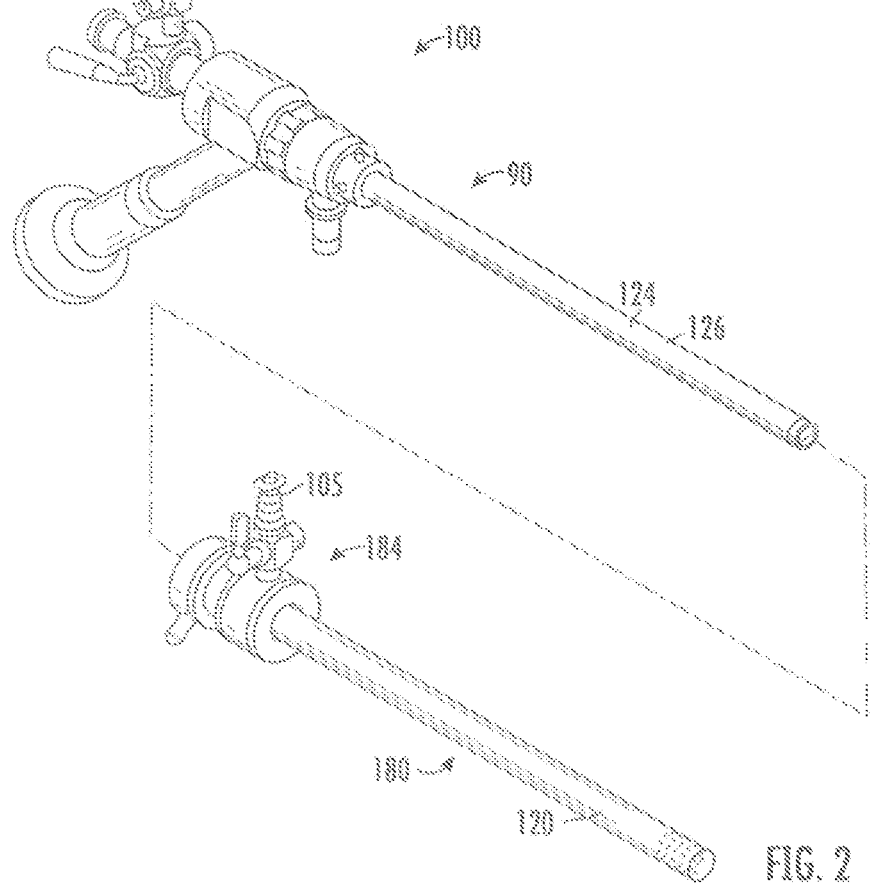
FIG. 2 is a perspective view of a hysteroscope connected to the fluid management system of FIG. 1.

Referring to FIG. 2, the outlet 50 of the output tube 30 is in fluid communication with a hysteroscope 100. Specifically, the outlet 50 is coupled to an inflow port 110 of the hysteroscope 100. Generally, the hysteroscope 100 includes a scope housing 90 that has an elongated member 124 and a sheath 180 having a tube 120. The elongated member 124 is receivable within the tube 120 of the sheath 180.

During a medical procedure, the sheath 180 is inserted into a body cavity, e.g., a uterus, to provide access to the body cavity and the elongated member 124 is inserted through the tube 120 to access the body cavity. The outlet 50 is coupled to the output tube 30 to fluidly connect the fluid reservoir 22 with the hysteroscope 100 such that as air pressure increases in the cuff 60, fluid is expelled from the fluid reservoir 22, through the hysteroscope 100, and into the body cavity to increase the volume or distend the body cavity to improve visualization of an interior of the body cavity.

For a detailed description of an exemplary hysteroscope reference may be made to U.S. Pat. No. 8,062,214, the entire contents of which are hereby incorporated by reference.

Figure 3:
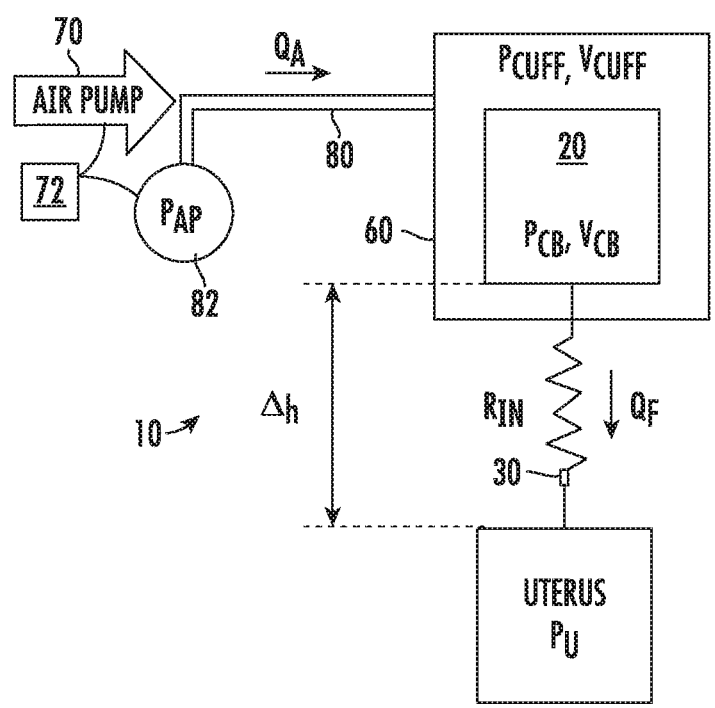
FIG. 3 is a schematic view of the fluid management system of FIG. 1.

With reference to FIGS. 1 and 3, the fluid management system 10 includes a controller 72 and a pressure sensor 82 for determining the pressure within the body cavity which is distended using the fluid management system 10. The pressure sensor 82 is in communication with the air hose 80 and is configured to determine the pressure within the air hose 80. The pressure sensor 82 may be operably coupled to or positioned within the air hose 80. The controller 72 is in communication with the pressure sensor 82 and receives signals from the pressure sensor 82 indicative of the pressure within the air hose 80. The controller 72 is also in communication with the air pump 70 and is configured to provide control signals to the air pump 70. The air pump 70 pumps air through the air hose 80 and into the cuff 60.

Figure 4:
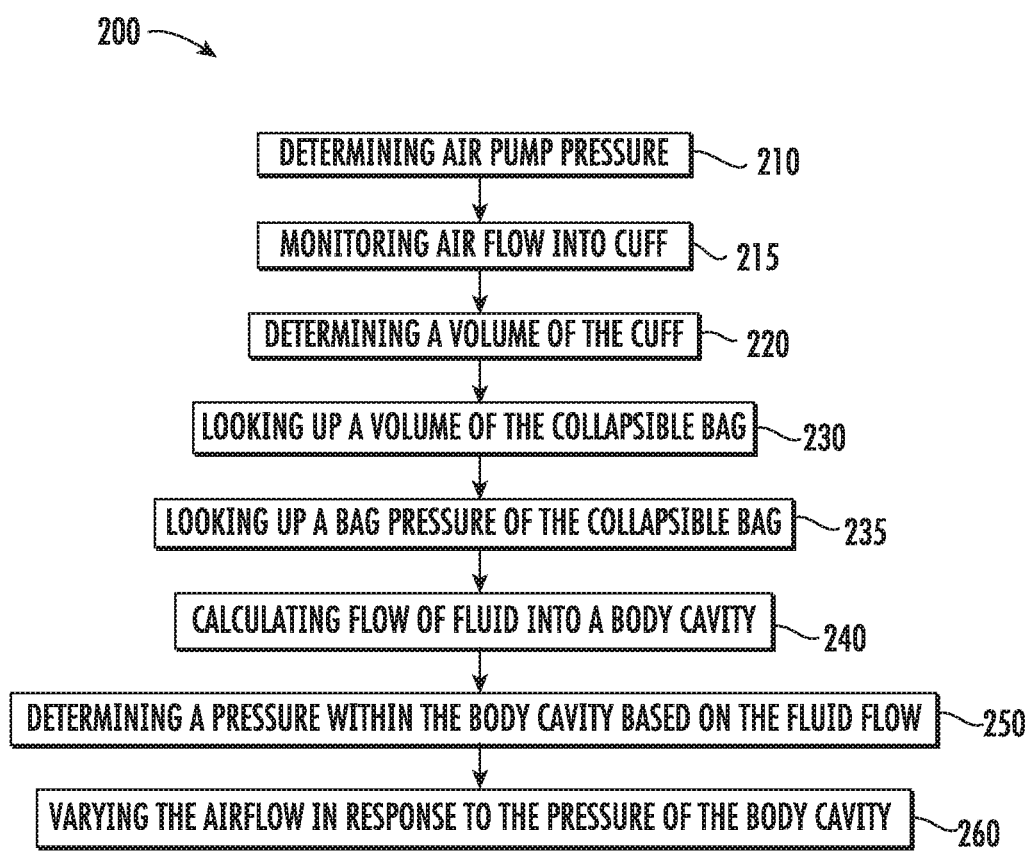
FIG. 4 is a flow chart of an exemplary method of determining a pressure of a body cavity.

Referring to FIG. 4, a method 200 of determining a pressure within a distended body cavity with the controller 72 is provided in accordance with the present disclosure with reference to the fluid management system 10 of FIGS. 1 and 3. The method 200 is discussed with reference to determining a uterine pressure $P_U$; however, the method 200 may be used to determine a pressure within other distendable organs or body cavities. The method 200 allows for monitoring a pressure within a distendable organ without an inline flow meter or a pressure sensor between the compressible bag 20 and the distendable organ. This may allow for a simplified system for distending an organ and monitoring a pressure within a distendable organ.

Figure 5:
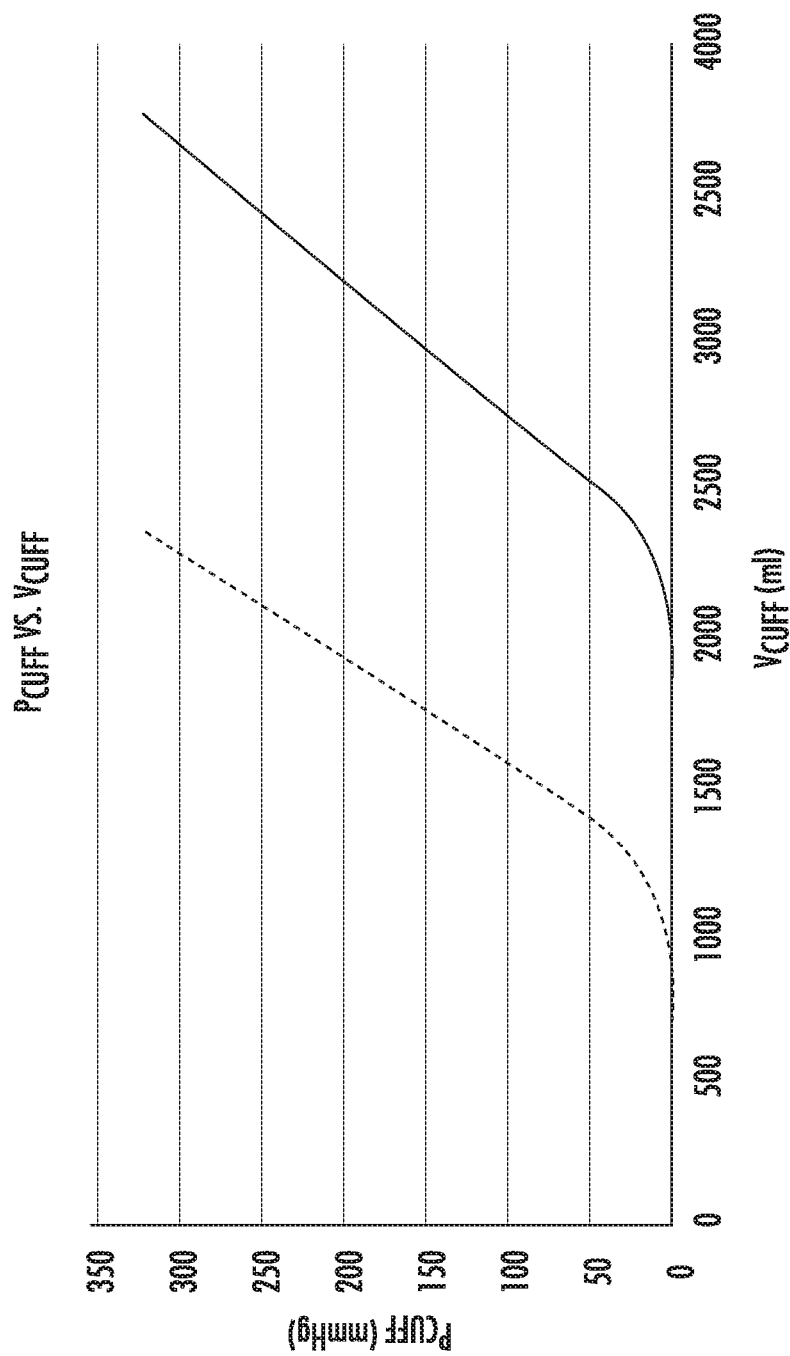
FIG. 5 is an exemplary graph of functions of cuff pressures and cuff volumes for given bag volumes.

Before determining a pressure of the body cavity, a relationship between a bag volume $V_{CB}$ of the compressible bag 20 from a cuff pressure $P_{CUFF}$ and a cuff volume $V_{CUFF}$ is determined empirically to form a reference graph for bag volume $V_{CB}$ as shown in FIG. 5. As shown, for each exemplary bag volume $V_{CB}$ a general relationship or function between cuff pressures $P_{CUFF}$ and cuff volumes $V_{CUFF}$ is determined.

Figure 6:
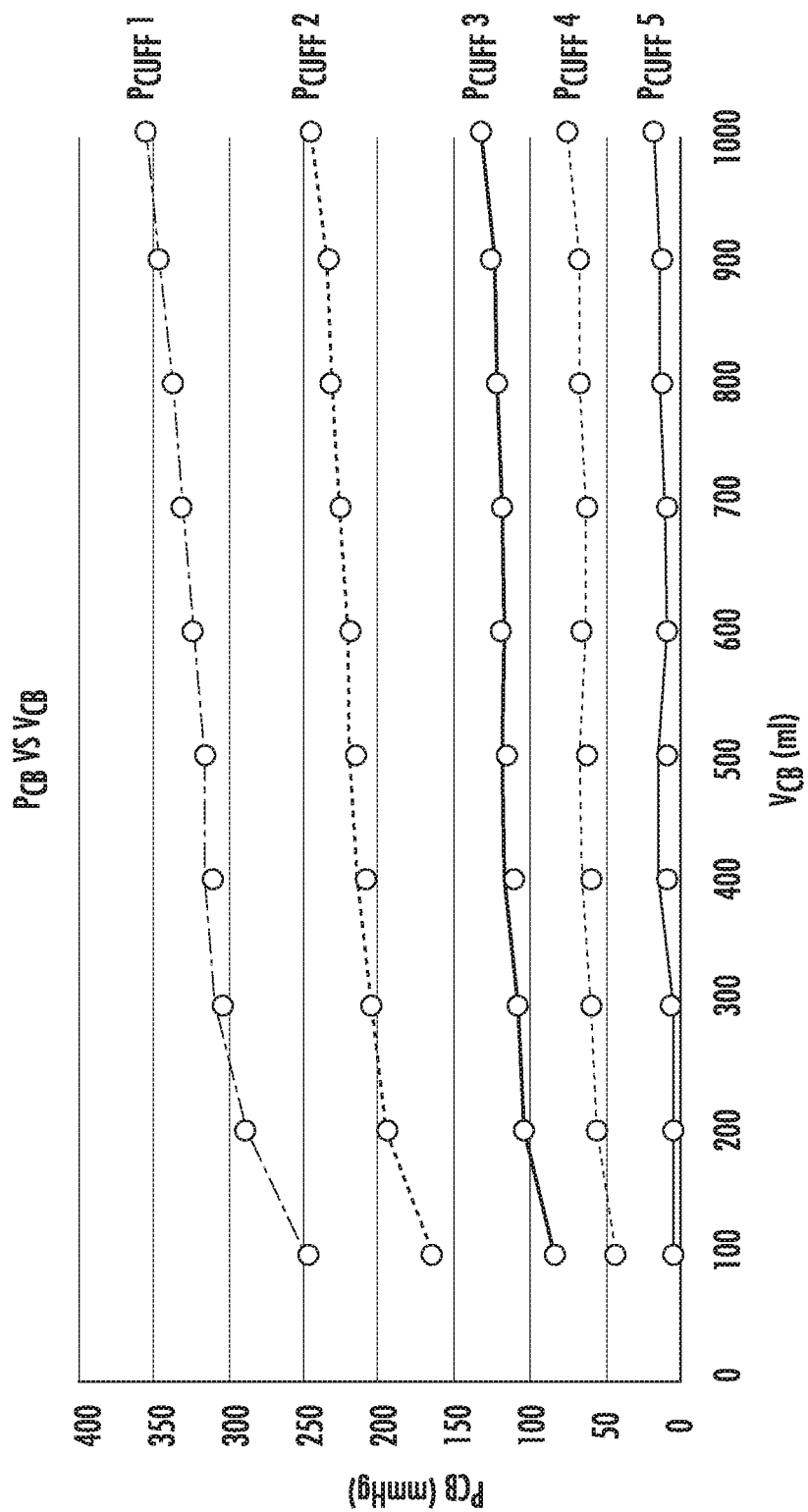
FIG. 6 is an exemplary graph of functions of bag pressures and bag volumes for given cuff pressures.

A bag pressure $P_{CB}$ within the compressible bag 20 can also be determined empirically for the cuff pressure $P_{CUFF}$ and cuff volume $V_{CUFF}$ as shown in FIG. 6. As shown, a general relationship between the bag pressure $P_{CB}$ and bag volume $V_{CB}$ for a given set of cuff pressure $P_{CUFF}$ and cuff volume $V_{CUFF}$ can be determined for each cuff pressure $P_{CUFF}$. The reference functions as shown in FIGS. 5 and 6 may be provided by the manufacturer of the fluid management system 10 or may be determined before a medical procedure through a system calibration. Specifically, reference functions may be preloaded in a memory of the controller 72.

Initially to determine the uterine pressure $P_U$, an air pump pressure $P_{AP}$ is determined using the pressure sensor 82 that is positioned in communication with the air hose 80 between the air pump 70 and the cuff 60 (Step 210). The air pump pressure $P_{AP}$ is determined in the first initial pumps of the air pump 70. When the pressure of the air pump $P_{AP}$ is static such that here is no instantaneous air flow within the air hose 80, the air pump pressure $P_{AP}$ is equal to the cuff pressure $P_{CUFF}$. The controller 72 also monitors an air flow $Q_A$ from the air pump 70 into the cuff 60 over time (Step 215) such that the control 72 determines the cuff volume $V_{CUFF}$ based on the cumulative air flow into the cuff 60 (Step 220).

With the cuff pressure $P_{CUFF}$ and the cuff volume $V_{CUFF}$ determined, the controller 72 utilizes a function as shown in FIG. 5, which may be loaded in memory, to determine a bag volume $V_{CB}$ of the compressible bag 20 (Step 230) based on the cuff pressure $P_{CUFF}$ and the cuff volume $V_{CUFF}$. Once the bag volume $V_{CB}$ is determined, the control 72 utilizes a function as shown in FIG. 6, which may be loaded in memory, to determine a bag pressure $P_{CB}$ (Step 235).

Once the bag volume $V_{CB}$ is determined, the controller 72 calculates a fluid flow $Q_F$ through the output tube 30 and into the uterus. The controller 72 determines the fluid flow $Q_F$ (Step 240) as follows:

$$Q_F = \frac{[V_{CB}(t) - V_{CB}(t - \Delta t)]}{\Delta t}$$

Once the fluid flow $Q_F$ is calculated, the uterine pressure $P_U$ can be determined (Step 250) as follows:

$$P_{CB} = P_U + Q_F R_{IN} = \rho g \Delta h$$

which is solved for uterine pressure $P_U$ as:

$$P_U = P_{CB} - Q_F R_{IN} + \rho g \Delta h$$

where resistance $R_{IN}$ of the output tube 30 and the height $\Delta h$ of the compressible bag 20 are known. The uterine pressure $P_U$ may be a quadratic function of the fluid flow $Q_F$. The equations above show a simplification of this quadratic function to a linear function which estimates the uterine pressure $P_U$ within a low margin of error. However, a quadratic function may be used for increased accuracy.

The controller 72 may include a display 74 that displays the uterine pressure $P_U$. In some embodiments, the display 74 may display an indication that the controller 72 is calibrating or determining a volume of the collapsible bag $V_{CB}$ such as "CAL" while the controller 72 is determining the cuff pressure $P_{CUFF}$, the cuff volume $V_{CUFF}$, and the bag volume $V_{CB}$. In embodiments, the controller 72 is in wireless communication to a portable electronic device, e.g., a smart phone, a tablet, a computer, such that the uterine pressure and/or the calibrating of the controller 72 is provided on the display. The controller 72 may also track a fluid volume of the compressible bag 20 and provide an signal, e.g., an audible or visual signal, to a clinician when a fluid volume of the compressible bag 20 is below an acceptable volume, e.g, when the compressible bag 20 is empty. Additionally or alternatively, the controller 72 may be in communication with a scale integrated into the compressible bag 20, e.g., hook 24, to track a weight, and thus a volume, of fluid within the compressible bag 20.

The air pump 70 may be a powered pump, e.g., an electric air pump. In such embodiments, the controller 72 may be in communication with the air pump 72 such that when the uterine pressure $P_U$ is known, the controller 72 may increase, maintain, or decrease the air flow $Q_A$ within the air hose 80 to increase, maintain, or decrease the uterine pressure $P_U$ in response to determining the uterine pressure $P_U$ to reach a desired uterine pressure $P_U$ (Step 260). The desired uterine pressure $P_U$ may be entered by a clinician or may be preselected for a selected organ which is inputted by the clinician.

Figure 7:
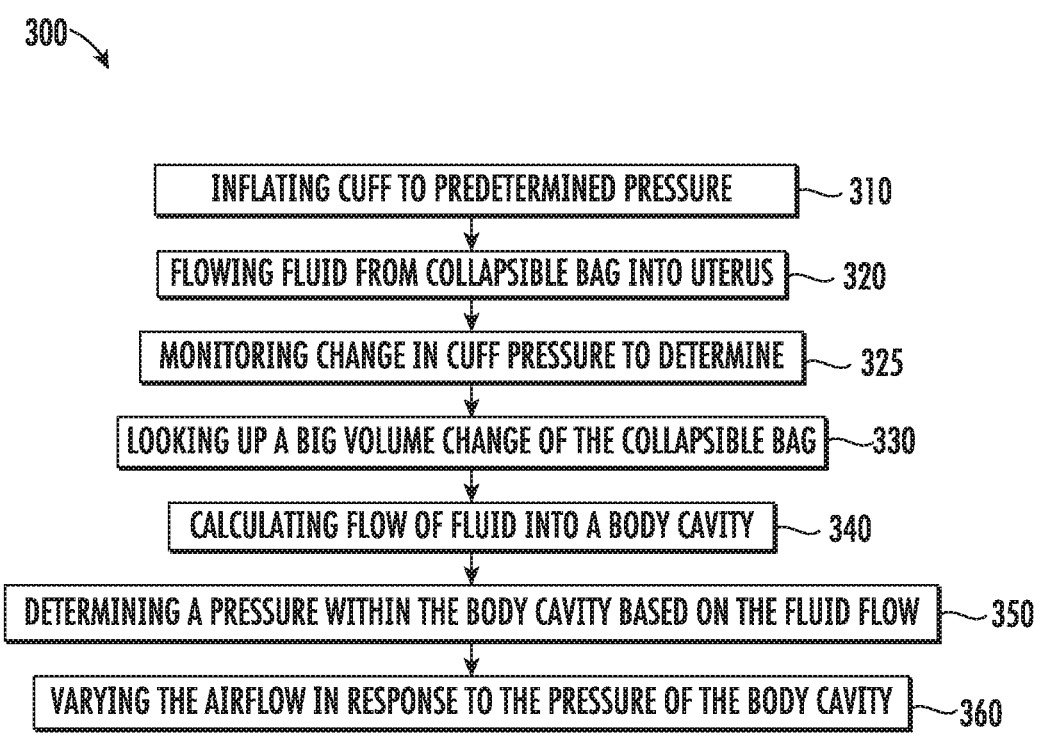
FIG. 7 is a flow chart of another exemplary method of determining a pressure of a body cavity.

With reference to FIG. 7, another method 300 for determining the pressure within a distendable body cavity is provided in accordance with the present disclosure with reference to the fluid management system 10 of FIGS. 1 and 3. The method 300 is discussed with reference to determining a uterine pressure $P_U$; however, the method 300 may be used to determine a pressure within other distendable organs or body cavities. The method 300 allows for monitoring a pressure within a distendable organ without an inline flow meter or a pressure sensor between the compressible bag 20 and the distendable organ. This may allow for a simplified system for distending an organ and monitoring the pressure within a distendable organ.

Figure 8:
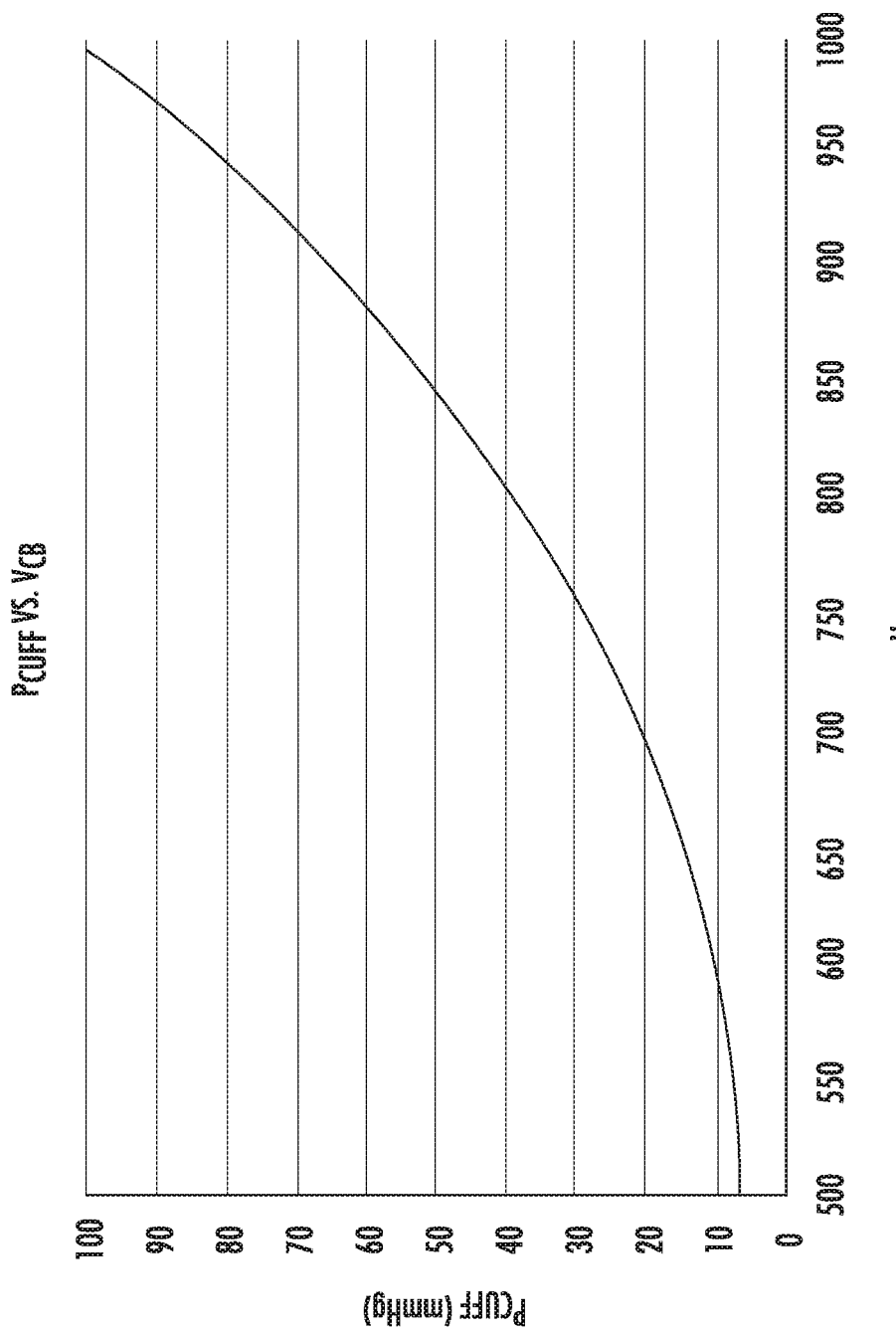
FIG. 8 is an exemplary graph of a function of cuff pressure and bag volume for an initial bag volume.

Before determining the pressure of the body cavity, a relationship between the bag pressure $P_{CB}$ of the compressible bag 20 and the cuff pressure $P_{CUFF}$ of the cuff 60 for combinations of cuff volumes $V_{CUFF}$ and bag volumes $V_{CB}$ are determined to empirically form a reference graph for bag volume $V_{CB}$ as a function of cuff pressure $P_{CUFF}$ as shown in FIG. 8. The function provides a general relationship between cuff pressure $P_{CUFF}$ and bag volumes $V_{CB}$. A reference function of FIG. 8 may be provided by the manufacturer of the fluid management system 10 and may be loaded in the controller 72 for use during a medical procedure. The reference function may be specific for each set of initial values of cuff pressure $P^0_{CUFF}$ and cuff volume $V^0_{CUFF}$.

Initially to determine the uterine pressure $P_U$, the air pump 70 is used to inflate the cuff 60 to a predetermined cuff pressure $P^1_{CUFF}$ (Step 310). The cuff pressure $P_{CUFF}$ may be measured by the pressure sensor 82 which is positioned in communication with the air hose 80 between the air pump 70 and the cuff 60.

When the cuff 60 reaches the predetermined cuff pressure $P^1_{CUFF}$, fluid is allowed to flow from the compressible bag 20 and into the uterus (Step 320). As the fluid flows from the compressible bag 20, the cuff pressure $P_{CUFF}$ decays over time as the bag volume $V_{CB}$ of the compressible bag 20 decreases and the cuff pressure change $\Delta P_{CUFF}$ is measured as fluid flows from the compressible bag 20 (Step 325).

Once the cuff pressure change $\Delta P_{CUFF}$ is determined, the controller 72 uses a reference function, e.g., as shown in FIG. 8, to determine the bag volume change $\Delta V_{CB}$ (Step 330). Once the bag volume change $\Delta V_{CB}$ is determined, the controller 72 calculates a fluid flow $Q_F$ from the compressible bag 20 (Step 340) as:

$$Q_F = \frac{[V_{CB}(t) - V_{CB}(t - \Delta t)]}{\Delta t}$$

Once the fluid flow $Q_F$ is calculated, the uterine pressure $P_U$ can be determined (Step 350) as follows:

$$P_{CB}=P_U+Q_F R_{IN}-pg\Delta h$$

which is solved for uterine pressure $P_U$ as:

$$P_U=P_{CB}-Q_F R_{IN}+pg\Delta h$$

where resistance $R_{IN}$ of the output tube 30 and the height $\Delta h$ of the compressible bag 20 are known.

The controller 72 may include a display 74 that displays the uterine pressure $P_U$. In some embodiments, the display 74 may display an indication that the controller 72 is calibrating or determining the fluid flow $Q_F$ such as "CAL" while the controller 72 is determining the fluid flow $Q_F$. In embodiments, the controller 72 is in wireless communication to a portable electronic device, e.g., a smart phone, a tablet, a computer, such that the uterine pressure and/or the calibrating of the controller 72 is provided on the display.

In some embodiments, the air pump 70 is a powered pump, e.g., an electric air pump. In such embodiments, the controller 72 may be in communication with the air pump 72 such that when the uterine pressure $P_U$ is known, the controller 72 may increase, maintain, or decrease the air flow $Q_A$ within the air hose 80 to increase, maintain, or decrease the uterine pressure $P_U$ in response to determining the uterine pressure $P_U$ to reach a desired uterine pressure $P_U$ (Step 360). The desired uterine pressure $P_U$ may be entered by a clinician or may be preselected for a selected organ which is inputted by the clinician.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of determining a pressure of a body cavity with a fluid management system, the method comprising:
    inflating a cuff to a predetermined pressure to apply pressure to a collapsible bag, wherein inflating the cuff includes manually pumping an air pump to inflate the cuff to the predetermined pressure;
    discharging fluid from the collapsible bag into the body cavity under the predetermined cuff pressure;
    measuring a change in pressure of the cuff as fluid flows from the collapsible bag into the body cavity;
    determining a bag volume change of the collapsible bag using a reference function based on the change in pressure of the cuff;
    calculating a fluid flow from the collapsible bag into a body cavity based on the determined bag volume change of the collapsible bag; and
    determining the pressure of the body cavity based on the fluid flow such that $$P_U=P_{CB}-Q_F R_{IN}+pg\Delta h,$$

wherein $P_U$ is the pressure of the body cavity,
$P_{CB}$ is a pressure of the collapsible bag,
$Q_F$ is the fluid flow from the collapsible bag,
$R_{IN}$ is a Resistance of output from the collapsible bag,
p is the fluid density,
g is gravity, and
$\Delta h$ is a height of the collapsible bag.

2. The method according to claim 1, wherein measuring the change in pressure of the cuff is in response to discharging the fluid from the collapsible bag.

3. The method according to claim 1, wherein a controller of the fluid management system determines the bag volume change from a memory of the controller.

4. The method according to claim 1, wherein inflating the cuff to the predetermined pressure includes measuring a pressure of the cuff with a pressure sensor disposed between the air pump and the cuff.

5. The method according to claim 4, wherein the air pump is a powered air pump.

6. The method according to claim 5, wherein measuring the pressure of the cuff with the pressure sensor includes increasing, maintaining, or decreasing an air flow within an air hose of the fluid management system increases, maintains, or decreases the pressure of the body cavity to reach the predetermined pressure via a controller.

7. The method according to claim 6, wherein the controller receives a preset predetermined pressure or an input predetermined pressure.

8. The method according to claim 1, wherein calculating the fluid flow from the collapsible bag includes subtracting a volume of the collapsible bag at a first time from a volume of the collapsible bag at a second time and dividing the result by the amount of time between the first and second time.

9. The method according to claim 1, further comprising providing the pressure of the body cavity on a display of a controller.

10. The method according to claim 9, further including displaying an indication of a state of the controller on the display of the controller.

11. The method according to claim 10, wherein the state of the controller is one of a calibrating state or a determining fluid flow state.

12. The method according to claim 1, further comprising transmitting a control signal to the air pump to pump air into the cuff in response to determining the pressure of the body cavity.

13. The method according to claim 1, wherein inflating the cuff to the predetermined pressure further includes permitting fluid to flow from the collapsible bag into the body cavity.

14. The method according to claim 13, wherein, as fluid flows from the collapsible bag into the body cavity, the pressure of the cuff decays over time with a decrease in a volume of the collapsible bag.

15. A method of determining a pressure of a body cavity with a fluid management system, the method comprising:
    inflating a cuff to a predetermined pressure to apply pressure to a collapsible bag;
    discharging fluid from the collapsible bag into the body cavity under the predetermined cuff pressure;
    measuring a change in pressure of the cuff as fluid flows from the collapsible bag into the body cavity;
    determining a bag volume change of the collapsible bag using a reference function based on the change in pressure of the cuff;
    calculating a fluid flow from the collapsible bag into a body cavity based on the determined bag volume change of the collapsible bag; and
    determining the pressure of the body cavity based on the fluid flow such that $$P_U=P_{CB}-Q_F R_{IN}+pg\Delta h,$$

wherein $P_U$ is the pressure of the body cavity, $P_{CB}$ is a pressure of the collapsible bag,
$Q_F$ is the fluid flow from the collapsible bag,
$R_{IN}$ is a Resistance of output from the collapsible bag,
p is the fluid density,
g is gravity, and
Δh is a height of the collapsible bag.

16. The method according to claim 15, wherein measuring the change in pressure of the cuff is in response to discharging the fluid from the collapsible bag.

17. The method according to claim 15, wherein a controller of the fluid management system determines the bag volume change from a memory of the controller.

18. The method according to claim 15, wherein inflating the cuff to the predetermined pressure includes measuring a pressure of the cuff with a pressure sensor disposed between an air pump and the cuff.

19. The method according to claim 15, wherein calculating the fluid flow from the collapsible bag includes subtracting a volume of the collapsible bag at a first time from a volume of the collapsible bag at a second time and dividing the result by the amount of time between the first and second time.

20. The method according to claim 15, further comprising providing the pressure of the body cavity on a display of a controller.

* * * * *